(12) United States Patent
Kauffman et al.

(10) Patent No.: US 7,713,452 B2
(45) Date of Patent: May 11, 2010

(54) COMPOUNDS THAT ABSORB ULTRAVIOLET LIGHT, METHODS OF THEIR PREPARATION AND OPTICAL LENSES CONTAINING THEM

(75) Inventors: Joel Kauffman, Wayne, PA (US); Peter T. Litak, Schwenksville, PA (US); Martin Rickwood, Clarks Green, PA (US)

(73) Assignee: Essilor International Compagnie Generale d'Optique, Charenton-le-Pont (FR)

(*) Notice: Subject to any disclaimer, the term of this patent is extended or adjusted under 35 U.S.C. 154(b) by 798 days.

(21) Appl. No.: 10/565,414

(22) PCT Filed: Dec. 30, 2005

(86) PCT No.: PCT/EP2005/014202

§ 371 (c)(1),
(2), (4) Date: Jan. 23, 2006

(87) PCT Pub. No.: WO2006/069811

PCT Pub. Date: Jul. 6, 2006

(65) Prior Publication Data

US 2008/0064880 A1    Mar. 13, 2008

Related U.S. Application Data

(60) Provisional application No. 60/640,506, filed on Dec. 30, 2004.

(51) Int. Cl.
*C07D 263/62* (2006.01)
*B29D 11/00* (2006.01)

(52) U.S. Cl. ............... 264/1.32; 264/1.6; 523/106; 523/135; 548/219; 548/220

(58) Field of Classification Search ............... 548/149, 548/219, 220, 301.7, 311.7; 523/106, 135; 264/1.32, 1.6
See application file for complete search history.

(56) References Cited

U.S. PATENT DOCUMENTS

| | | | |
|---|---|---|---|
| 5,298,189 A | 3/1994 | Kauffman | 252/301.17 |
| 5,587,112 A | 12/1996 | Kauffman et al. | 252/589 |

OTHER PUBLICATIONS

Yang, Nam C. An iodide sensory property of a strongly blue-fluorescent polycationic molecular wire from a new polybenzimidazole. Polymer Bulletin. 49 (2003) 371-377.*

Patani, George A., Bioisosterism: A rational approach in drug design. Chem. Rev. 96 (1996) 3147-3176.*

Belfield, Kevin D. Synthesis, Characterization, and Optical Properties of New-Two-Photon-Absorbing Fluorene Derivatives. Chem. Mater. 16 (2004) 4634-4641.*

(Continued)

*Primary Examiner*—Kamal A Saeed
*Assistant Examiner*—Samantha L Shterengarts
(74) *Attorney, Agent, or Firm*—Fulbright & Jaworski, L.L.P.

(57) ABSTRACT

Compounds that absorb ultraviolet light 380 nm to 400 nm range but avoid absorption in the blue light range, thereby imparting yellowness, i.e., 410-420 nm have suitable refractive characteristics useful in the preparation of optical resins or plastics suitable, for example, for the manufacture of ophthalmic lenses. Methods for making the compounds, optic lenses containing the compounds, and methods for making these are also described.

20 Claims, 3 Drawing Sheets

OTHER PUBLICATIONS

Preston et al., "Heterocyclic intermediates for the preparation of thermally stable polymers. II. Benzoxazoles and Benzothiazoles," *Journal of Heterocyclic Chemistry*, 5:269-273, 1968.

Reiser et al., "Fluorescence of aromatic benzoxazole derivatives," *Journal of the American Chemical Society*, 94:2414-2421, 1972.

* cited by examiner

COMPOUNDS THAT ABSORB ULTRAVIOLET LIGHT, METHODS OF THEIR PREPARATION AND OPTICAL LENSES CONTAINING THEM

This application is a national phase application under 35 U.S.C. §371 of International Application No. PCT/EP2005/014202 filed 30 Dec. 2005, which claims priority to U.S. Provisional Application No. 60/640,506 filed 30 Dec. 2004. The entire text of each of the above-referenced disclosures is specifically incorporated herein by reference without disclaimer.

BACKGROUND OF THE INVENTION

1. Field of the Invention

The present invention relates to compounds that absorb ultraviolet light 380 nm to 400 nm range while avoiding absorption in the yellow light range, i.e., 410-420 nm having suitable refractive characteristics useful in the preparation of optical resins or plastics suitable, for example, for the manufacture of ophthalmic lenses.

The present invention is also directed to methods of making these compounds, polymeric blends containing such compounds, optical devices containing the compounds, and methods for preparing these optical devices.

2. Description of Related Art

In recent years, transparent synthetic resins have found increasing applications as optical plastic materials replacing inorganic optical materials because of their light weight and good impact strength, moldability or processability and dyeability.

Plastics used in the preparation of optical devices must have properties suitable for the intended purpose. These materials should, inter alia, be transparent, non-yellowing, and have a suitable refractive index. In general, the higher the refractive index polymer allows for a thinner more lightweight lens, as well as an improved physical appearance. A refractive index of 1.5 or greater is desired, and higher refractive index plastics, e.g., 1.6, 1.7, 1.8 or more, are preferred.

The dangers of ultraviolet light to eyes is well-documented. Therefore, there have been many attempts to make and commercialize optical plastic materials that filter out ultraviolet light. Many such attempts have involved the incorporation of compounds that absorb ultraviolet light into the plastic material.

Ultraviolet absorbent plastics are well-know in the art. For example, U.S. Pat. No. 5,298,189 to Kauffman describes proton transfer, bis-benzoxazole, fluorescent compounds, i.e., fluors that include substituted or unsubstituted 1,4-bis(2-benzoxazolyl)-2-hydroxybenzenes and 1,4-bis(2-benzoxazolyl)-2-amidobenzenes that absorb ultraviolet light in the 300-420 nm range and fluoresce in the 480 to 560 nm range. These are said to be useful in organic scintillator systems.

U.S. Pat. No. 5,587,112 to Kauffman et al. discloses a class of proton transfer, 2-benzoxazolyl moieties covalently bound to an aromatic fused ring heterocyclic moiety. These compounds absorb ultraviolet light in the 420 nm or shorter, e.g., 300 to 420 nm range, and fluoresce in the 520 nm to 800 nm range. These compounds are said to be useful in the manufacture of fluorescent coatings, objects, scintillators, light sources and the like.

However, such previous ultraviolet absorbers have a propensity towards absorbing yellow light in the 410 to 420 nm range, which leads to a yellow color of a lens containing such absorbers. To obtain maximum ultraviolet absorption while avoiding yellowing, a lens should absorb ultraviolet light in the 380 nm to 400 nm range while avoiding absorption in the yellow light range, i.e., 410 to 420 nm. However, obtaining such a sharp "cut" or reduction on the absorbance ability of an ultraviolet absorber in such a narrow range has not proven easy, and ultraviolet absorbers exhibiting the preferred ultraviolet absorption in the 380 to 400 nm range without absorption in the 410 to 420 nm range are not taught or suggested in the aforementioned patents.

New polymers having such absorption qualities are desirable for use as, inter alia optical lenses, as these would avoid undesirable yellowing.

SUMMARY OF THE INVENTION

It is an object of this invention, therefore, to provide compounds which can absorb ultraviolet light in the 380 to 400 nm range, but do not or do not substantially absorb light in the 410 to 420 nm range useful as an optical plastic material.

Preferably, these compounds absorb, when compounded into suitable optical products, such as an ophthalmic lens, at least 90% of UV light in the 380-400 nm range. Even more preferably, they absorb 95% of UV light in the 380-400 nm range. Most preferred embodiments absorb 96%, 97%, 98%, 99%, 99.5% 99.9% and/or more U light in the 380-400 nm range. Further, the compounds preferably absorb less than 10% of light in the 410-420 range. Even more preferably, they absorb only or less than 5%, 4%, 3%, 2%, 1%, and/or 0.5% of light in the 410-420 nm range, with less absorbance in the latter range being more preferred. Preferably, these compounds also can be incorporated into a optical polymer systems and result in lenses that have a high refractive index and excellent transparency.

In preferred embodiments, the present invention relates to ultraviolet absorbent compounds for use in preparing optical plastics which have a suitable refractive index. For example, in broad aspects the invention relates to compounds of the Formula 1, as described in the Detailed Description.

Preferred compounds of the invention include 2-hydroxyphenyl(benzoxazol-2-yl) derivatives of Formula 2 as described in the Detailed Description, for example, those compounds having a formula of Formula 3 and Formula 4. Other preferred compounds are shown in Formula of the Detailed Description.

By adding the compounds of the present invention to other polymers, e.g., polycarbonate, various compounds can be made having ultraviolet light absorbing characteristics as described above. The polymer blends containing the UV-absorbers of the invention preferably have a high refractive index and excellent transparency, and have good processability characteristics such as machinability, and are suitable as optical plastics.

Preferably the polymer blends contain approximately 0.0001% to 1% UV absorber by total weight of the polymer blend, which 0.001% to 0.5% being more preferred in some embodiments.

Methods for producing these compositions and optical lenses prepared from these compositions are also a part of the present invention. Those of skill in the art will know how to make these compounds using techniques known in the art.

In a preferred embodiment, the compounds of the invention are prepared by forming an intermediate compound of Formula 6 as described below and using them to make compounds of Formula 7.

Optical lenses may be prepared by preparing a blend containing the UV-absorbers of the present invention with other polymers, e.g., polycarbonate, CR39 (a polymer of a diethyleneglycol bisallylcarbonate monomers), or other polymers and forming an optical lens from the blend using traditional techniques. Optical lenses comprising the compounds are also a part of the invention.

In some aspects of the invention, the compounds of the present invention may be added to thermoset resins (e.g. CR39) may alone or in conjunction with known UV absorbers to provide suitable coverage for any UV wavelengths in any region outside the range of the UV absorbing compounds of the present invention, typically in the 200-370 nm region. This is commonly called "backfilling".

DETAILED DESCRIPTION

Figure 1:
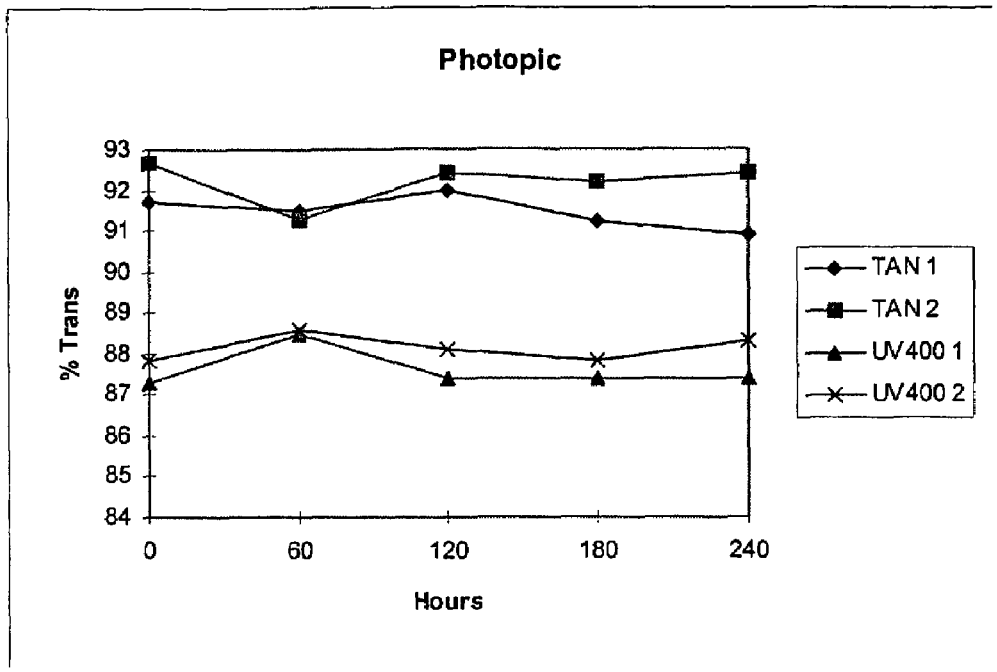
FIG. 1 is a graph of photopic comparative data shown Table 1.

The invention relates to compounds of the Formula 1:

$$X\text{—}Y\text{—}Z \qquad \text{Formula 1}$$

wherein Y is an aromatic cyclic structure substituted at least once with OH and optionally with SH, H, $C_{1\text{-}22}$ alkyl, $C_{2\text{-}22}$ alkene, $C_{2\text{-}22}$ alkyne, primary, secondary or tertiary amine, amino, nitro, nitroso, halogen, and at least one of X and Z are a carbon-containing ring structure that may also contain at least one of oxygen, nitrogen and sulfur. Preferably, X and Z are independently selected from H, nitro, nitroso, cyano, halogen, $C_{1\text{-}22}$ alkyl, $C_{1\text{-}22}$ alkoxy, —C(O)$R^9$ wherein $R^9$ is $C_{1\text{-}8}$ alkyl, —O—C—O—$R^9$ wherein $R^9$ is $C_{1\text{-}8}$ alkyl, —COO$R^{10}$ wherein $R^{10}$ is H or $C_{1\text{-}8}$ alkyl, —C(O)N$R^{10}$ wherein $R^{10}$ is H or $C_{1\text{-}8}$ alkyl, a primary, secondary or tertiary amine, substituted or unsubstituted carbocyclic ring, a substituted or unsubstituted aryl ring, a substituted or unsubstituted heteroaryl ring, a substituted or unsubstituted benzannulated carbocyclic ring, a substituted or unsubstituted benzannulated heterocyclic ring, a substituted or unsubstituted arylannulated carbocyclic ring or a substituted or unsubstituted arylannulated heterocyclic ring. Preferably at least one of X and Z are a substituted or unsubstituted benzoxazole, benzothiazole, or benzimidazole.

The inventive compounds absorb ultraviolet light in the 380 nm to 400 nm range but have less than 10% absorption in the 410-420 nm range.

Preferred compounds include 2-hydroxyphenyl(benzoxazol-2-yl) derivatives of Formula 2 below:

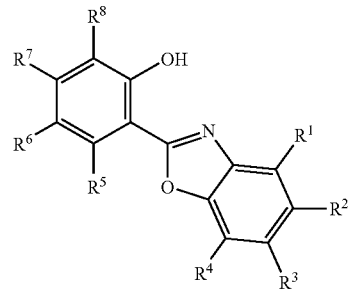

Formula 2 wherein $R^1$, $R^2$, $R^3$ and $R^4$ are independently selected from H, alkyl ($C_1$-$C_8$), alkoxy ($C_1$-$C_8$), acyl (—C(O)R; R=alkyl $C_1$-$C_8$), acetoxy (—OC(O)R; R=alkyl $C_1$-$C_8$), carboxylic acid and esters (—$CO_2$R=H or alkyl of $C_1$-$C_8$), amine (N$R_2$; R=H or alkyl $C_1$-$C_8$), nitro, nitroso, cyano, halogen (Cl, Br, I or F), substituted or unsubstituted aryl, substituted or unsubstituted heteroaryl, amide (—C(O)N$R_2$ R=H or alkyl $C_1$-$C_8$), or wherein $R^1$ and $R^2$ or $R^2$ and $R^3$ or $R^3$ and $R^4$ together form a carbocyclic ring, substituted or unsubstituted and fused carbocyclic ring, substituted or unsubstituted benzannulated carbocyclic and substituted or unsubstituted arylannulated carbocyclic; and $R^5$, $R^6$, $R^7$ and $R^8$=H, alkyl ($C_1$-$C_8$), alkoxy ($C_1$-$C_8$), acyl (—C(O)R; R=alkyl $C_1$-$C_8$), acetoxy (—OC(O)R; R=alkyl $C_1$-$C_8$), carboxylic acid and esters (—$CO_2$R=H or alkyl of $C_1$-$C_8$), amine (N$R_2$; R=H or alkyl $C_1$-$C_8$), nitro, nitroso, cyano, halogen (Cl, Br, I or F), substituted or unsubstituted aryl, substituted or unsubstituted heteroaryl, amide (—C(O)N$R_2$ R=H or alkyl $C_1$-$C_8$), substituted or unsubstituted heterocyclic, substituted or unsubstituted benzannulatedheterocyclic and substituted or unsubstituted arylannulated heterocyclic; or $R^5$ and $R^6$ or $R^6$ and $R^7$ or $R^7$ and $R^8$ together form a carbocyclic ring, substituted or unsubstituted benzannulated carbocyclic and substituted or unsubstituted arylannulated carbocyclic.

Particularly preferred compounds of the present invention preferably have the Formula 3:

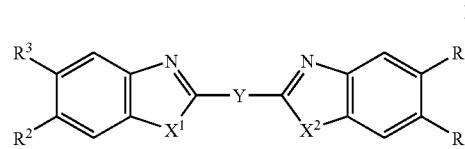

Formula 3 wherein:

$X^1$ and $X^2$ are independently selected from N, S or O, preferably O in some embodiments;

Y is an aromatic carbocyclic or heterocyclic moiety substituted at least once with OH and optionally substituted with, SH, H, $C_{1\text{-}22}$ alkyl, $C_{2\text{-}22}$ alkene, $C_{2\text{-}22}$ alkyne, primary, secondary or tertiary amine, nitro, nitroso, halogen;

$R^2$, $R^3$, $R^{12}$ and $R^{13}$ are independently a substituted or unsubstituted, straight or branched $C_{1\text{-}22}$ alkyl, $C_{2\text{-}22}$ alkene, $C_{2\text{-}22}$ alkyne, phenyl, $C_{3\text{-}6}$ cycloalkyl;

wherein $R^2$ and $R^3$ together or $R^{12}$ and $R^{13}$ form an aromatic or nonaromatic 1 to 3 ring cyclic structure.

Preferably, Y is further substituted with other groups such as hydrogen, a substituted or unsubstituted, straight or branched $C_{1-22}$ alkyl, $C_{2-22}$ alkene, $C_{2-22}$ alkyne, phenyl, $C_{3-6}$ cycloalkyl.

Preferably, at least one of the pairs $R^2$ and $R^3$ together or $R^{12}$ and $R^{13}$ form

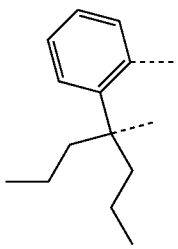

to provide a compound such as that shown in Formula 4:

Formula 4

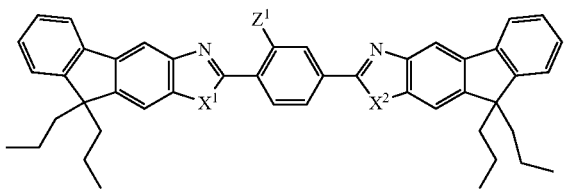

wherein X is O, N or S; and Z is OH, SH, or $NH_2$. Preferably Z is OH or X is O.

In another preferred embodiment, Y in Formula 3 is

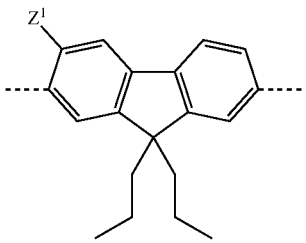

wherein $Z^1$ is OH, primary or secondary amine, or SH.

An example of such a compound is shown in Formula 5 below:

Formula 5

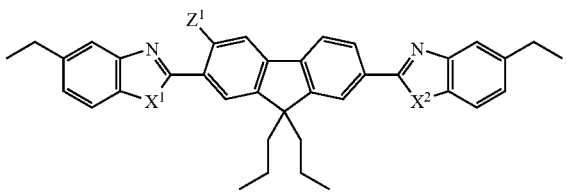

wherein $X^1$ and $X^2$ are independently O, N or S, preferably O in some embodiments, and $Z^1$ is as defined above.

It is preferred that the branched alkyls on the Y group of Formula 3 are $C_1$-$C_{10}$ alkyls, or more preferably $C_{11}$-$C_{22}$ alkyls. The alkyls may be aliphatic or branched, substituted, e.g., with halogen, or unsubstituted. $C_1$ to $C_3$ aliphatic or $C_3$ to $C_6$ branched alkyls are preferred.

It is preferred that the compounds according to the present invention have a UV light absorbance of at least 95% in the 380-405 nm range and also an absorbance of less than 5% in the 410-420 nm range. More preferably, the compounds absorb greater than 95% UV light in the 385-400 range, and more preferably in the 390-405 nm range.

Particularly preferred species are described in the examples.

Optimally, there is no absorbance in the 410-420 nm range, but less than, 10% absorbance is required, less than 5% is preferred, and 1-3% is most preferred.

The UV absorbers of the present invention can be incorporated into or onto any organic glass substrate currently used for organic ophthalmic lenses, including but not limited to thermoplastic lenses. Such incorporation can be done by mixing the UV absorbers with monomers prior to polymerizing them into an organic glass containing the absorber. Alternatively, the UV absorbers may be incorporated into a coating and deposited on a polymerized organic glass.

Polycarbonate (thermoplastic) substrates, in particular the ophthalmic lenses manufactured by the Gentex Optics company, are examples of such substrates. Among other suitable substrates are the substrates obtained by the polymerization of alkyl methacrylates such as methyl (meth)acrylate and ethyl (meth)acrylate, allyl derivatives such as the allyl carbonates of linear or branched aliphatic or aromatic polyols, thio(meth)acrylics, thiourethanes, polyethoxylated aromatic (meth)acrylates such as the polyethoxylated bisphenolate dimethacrylates.

Recommended substrates include substrates obtained by polymerization of the allyl carbonates of polyols such as ethylene glycol bis(allyl carbonate), diethylene glycol bis(2-methyl carbonate), diethylene glycol bis(allyl carbonate), ethylene glycol bis(2-chloroallyl carbonate), triethylene glycol bis(allyl carbonate), 1,3-propanediol bis(allyl carbonate), propylene glycol bis(2-ethylallyl carbonate), 1,3-butenediol bis(allyl carbonate), 1,4-butenediol bis(2-bromoallyl carbonate), dipropylene glycol bis(allyl carbonate), trimethylene glycol bis(2-ethylallyl carbonate), pentamethylene glycol bis(allyl carbonate), isopropylene bisphenol A bis(allyl carbonate).

Some substrates that are particularly recommended are substrates obtained by polymerization of ethylene glycol bis(allyl carbonate), sole under the trade name CR 39® by the company PPG Industries (lens ORMA® ESSILOR).

Among other recommended substrates are substrates obtained by polymerization of thio(meth)acrylic monomers.

The UV absorber/plastic blend will have a UV absorbance of that will be a result of the combination of the absorbance of the UW absorber and any absorbance of the plastic.

The compositions of the present invention may have one or more chiral centers and may have enantiomers and diastereoisomers that are contemplated to be within the scope of the present invention.

In a preferred embodiment, the compounds of the invention are prepared by forming an intermediate compound of Formula 6:

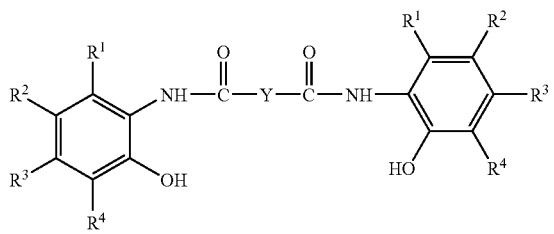

and reacting the formula under suitable conditions and with suitable reagents to form a compound of the formula:

Formula 7

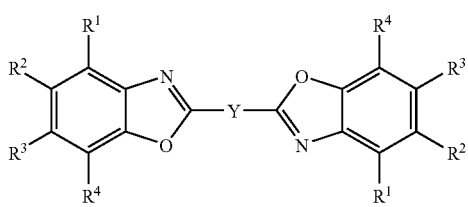

wherein Y and R¹—R⁴ are defined above.

Preferred embodiments of the invention are discussed in detail in the Examples below.

Preparation Of Preferred UV Absorbent Compounds

EXAMPLE 1

Preparation of 1,4-Bis(9,9-dipropyl-9H-fluoreno[3,2-d]oxazol-2-yl)-2-hydroxyphenyl

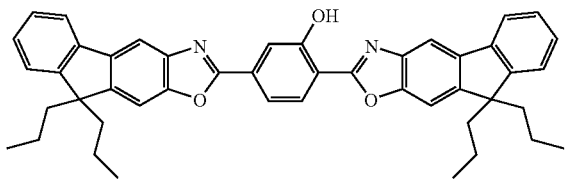

Step 1. Preparation of 2-Methoxy-N,N'-Bis(2-hydroxy-9,9-dipropyl-2-methoxyfluoren-3-yl)-1,4-benzenedicarboxamide

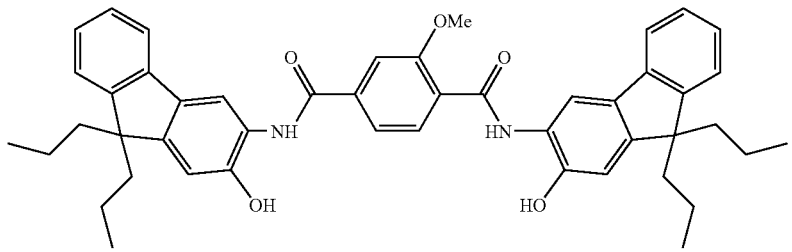

A mixture of methoxyterephthalic acid (1.50 g, 7.65 mmol), thionyl chloride (1.23 mL, 2.00 g, 16.8 mmol) and N-methylpyrrolidine (1.0 mL) in tetrahydrofuran (50.0 mL) was heated under reflux for 5 hours to form methoxyterephthaloyl chloride in-situ. The formed methoxyterephthaloyl chloride solution was cooled and added drop-wise to a solution of 3-amino-9,9-dipropyl-2-hydroxyfluorene (5.00 g, 16.8 mmol), pyridine (2.65 g, 33.6 mmol) and tetrahydrofuran (150 mL) and stirred under nitrogen at room temperature for 18 hours. The resulting mixture was treated with concentrated hydrochloric acid (10.0 mL) and stirred for 15 min. The crude product was collected, washed with water and then slurried with methanol (75.0 mL), stirred for 30 min. and filtered. The collected solid was slurried for 30 min. with a mixture of methanol (100 mL) and 5% aqueous sodium bicarbonate (50.0 mL). The filtered solid was slurrried once more, for a further 30 min. with methanol (100 mL), collected, washed with methanol and dried to yield 2-methoxy-N,N'-bis(2-hydroxy-9,9-dipropyl-2-methoxyfluoren-3-yl)-1,4-benzenedicarboxamide (4.01 g, Yield 69%).

Analytical Results were as follows: Melting point, 262-266° C.

Step 2. Preparation of 1,4-Bis(9,9-dipropyl-9H-fluoreno[3,2-d]oxazol-2-yl)-2-methoxyphenyl.

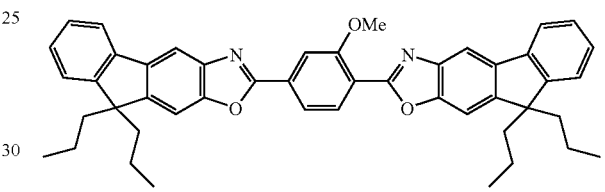

A magnetically stirred mixture of 2-methoxy-N,N'-bis(2-hydroxy-9,9-dipropyl-2-methoxyfluoren-3-yl)-1,4-benzenedicarboxamide (3.75 g, 4.97 mmol), powdered boric acid (0.1 g), and diethylene glycol dibutyl ether (60.0 mL) under nitrogen was heated to reflux for 45 min. with removal of water. The resulting mixture was then concentrated with removal of solvent (40.0 mL), allowed to cool to below 60° C., poured into hexane (120 mL) and stored for 18 hours at −20° C. The mixture was filtered and dried to yield crude product (2.96 g, yield 85%). Purification by extraction from neutral alumina (3 cm³) with heptane on an Ace-Kauffman column yielded 1,4-bis(9,9-dipropyl-9H-fluoreno[3,2-d]oxazol-2-yl)-2-methoxyphenyl as yellow needles (2.10 g; yield 59%).

Analytical Results were as follows: Melting point 210-213° C.

Step 3. Preparation of 1,4-Bis(9,9-dipropyl-9H-fluoreno[3,2-d]oxazol-2-yl)-2-hydroxyphenyl.

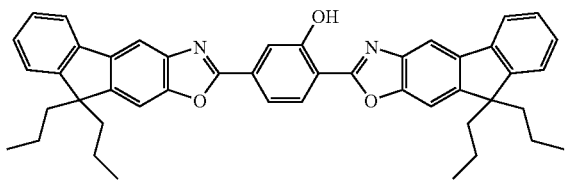

A mixture 1,4-bis(9,9-dipropyl-9H-fluoreno[3,2-d]oxazol-2-yl)-2-methoxyphenyl (1.94 g, 2.70 mmol), anhydrous lithium iodide (0.63 g, 4.72 mmol) and 2,4,6-collidine (30.0 mL) stirred under nitrogen, was heated under reflux for 4 hours. The resulting mixture was poured into water (150 mL), treated with hydrochloric acid (20.0 mL), stirred for 15 min. and filtered. The collected solid crude product was added to 5% sodium bicarbonate (200 mL), stirred, filtered washed with water and dried under vacuum to obtain crude 1,4-bis(9,9-dipropyl-9H-fluoreno[3,2-d]oxazol-2-yl)-2-hydroxyphenyl. Purification by extraction from neutral alumina (2 cm³) on an Ace-Kauffinan column, with toluene (60.0 mL) overnight, concentration of the extract, suspension of the residue in hot heptane, then cooling gave the product as yellow solid, 1.28 g (67%). Further purification by way of soxhlet extraction using ethyl acetate afforded 1,4-bis(9,9-dipropyl-9H-fluoreno[3,2-d]oxazol-2-yl)-2-hydroxyphenyl as a yellow solid (1.15 g yield 60%).

Analytical Results were as follows: M. pt. 330-331.5°.

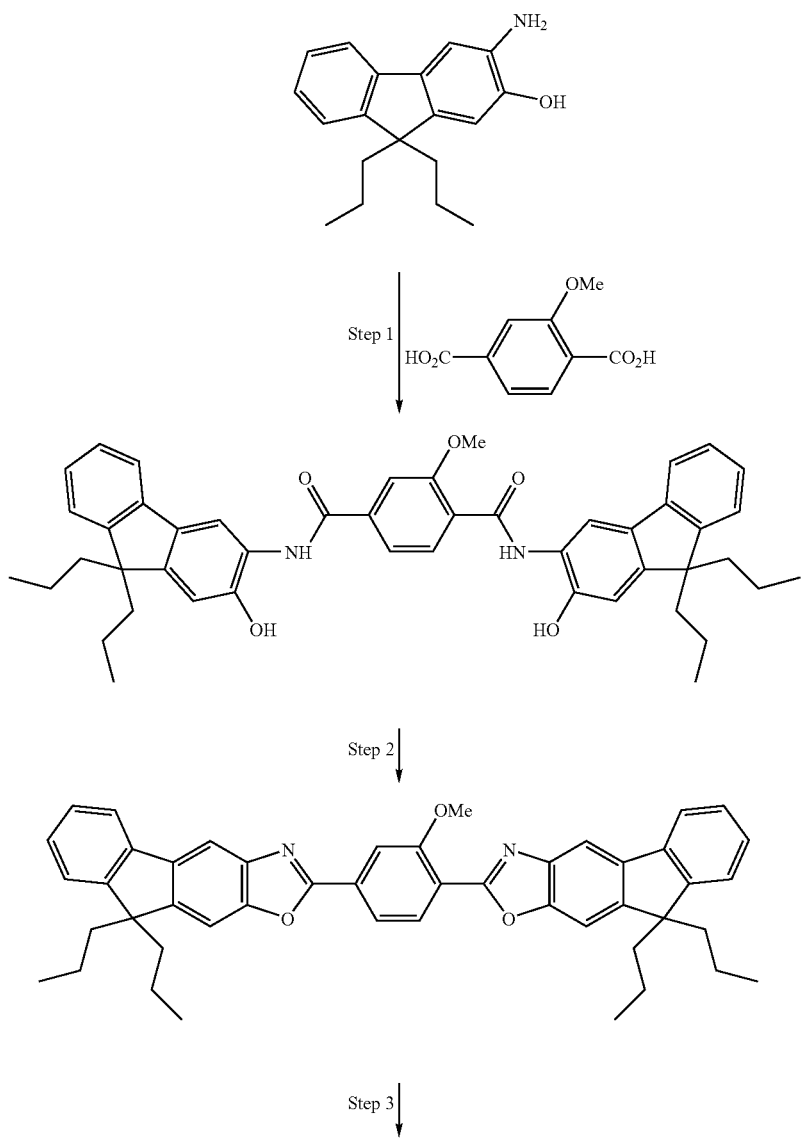

Reaction Scheme Example 1

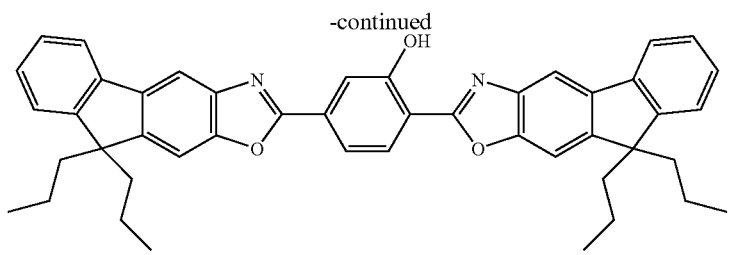

EXAMPLE 2

Preparation of 2,7-Bis(5-methylbenzoxazol-2-yl)-9,9-dipropyl-3-hydroxyfluorene

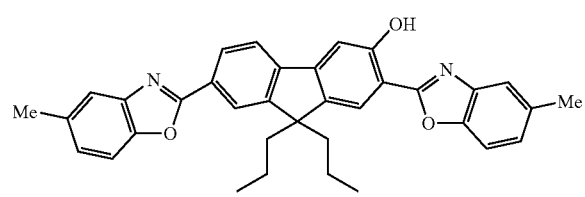

Step 1. Preparation of 2,7-Dibromo-3-methoxyfluorene.

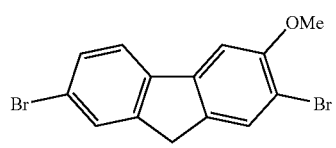

A stirred solution 3-methoxyfluorene (66.3 g, 0.34 mol) and dichloromethane (650 mL) was treated drop-wise with a portion of a solution of bromine (34.3 mL, 106 g, 0.667 mol) and dichloromethane (34.3 mL) at room temperature to initiate a reaction. The reaction was then cooled to −2° C. and the reminder of the bromine-dichloromethane solution added over 2 hours. The resulting slurry was stirred for a further 30 min. then diluted with methanol (1300 mL) and stored under refrigeration for 3 days. The product was collected, washed with methanol (300 mL) and dried under vacuum to yield crude product (89 g) as an off white solid, m. pt. 169-172° C. Purification by recrystallization (1-butanol) afforded 2,7-dibromo-3-methoxyfluorene (86.4 g, yield 71%).

Analytical Results were as follows: M. pt. 171.5-172.5° C. Analytical Calculation: C, 47.50; H, 2.85; Br, 45.14%. Found: C, 47.75; H, 2.65; Br, 47.00%. $^1$Hnmr (200 MHz, CDCl$_3$): ☐=3.78 (2H, sl br s, H9), 4.00 (3H, s, CH$_3$O), 7.49 (1H, dd, $J_{5,6}$=8.1 Hz, $J_{6,8}$=1.7 Hz, H6), 7.58 (1H, dd, $J_{5,8}$=0.5 Hz, H5), 7.64 (1H, dd, $J_{8,9}$=0.8 Hz, H8), 7.67 (1H, sl br d, $J_{1,9}$=0.9 Hz, H1).

Step 2. Preparation of 2,7-Dibromo-9,9-dipropyl-3-methoxyfluorene

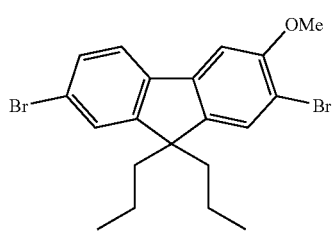

To a stirred mixture of 2,7-dibromo-3-methoxyfluorene (87.7 g, 0.244 mol), potassium t-butoxide (28 g, 0.25 mol) and dry methyl sulfoxide (500 mL) was added 1-bromopropane (22.6 mL, 0.25 mol) at such a rate as to keep the reaction exotherm temperature below 45° C. A further quantity of potassium t-butoxide (39.0 g; 0.35 mol) and 1-bromopropane (31.6 mL; 0.35 mol) were added. The resulting mixture was stirred at room temperature for 1 hour and treated with 50% methanol/water (500 mL). The purple color was discharged by addition of 6.0M hydrochloric acid (2.0 mL) and the mixture cooled at 0° C. for 1 hour. The crude product was collected and washed with 50% methanol/water (250 mL) and dried to yield crude product (106 g). Purification by extraction from neutral alumina (5 cm$^3$) with hexane on an Ace-Kauffman column with hexane afforded 2,7-dibromo-9,9-dipropyl-3-methoxyfluorene (95 g; m. pt. 127-131.5° C.). Further purification by re-crystallization (2-propanol) gave pure product (84 g, yield 78%).

Analytical Results were as follows: M. pt, 130.5-133.5° C.

Step 3. Preparation of 2,7-Dicyano-9,9-dipropyl-3-methoxyfluorene

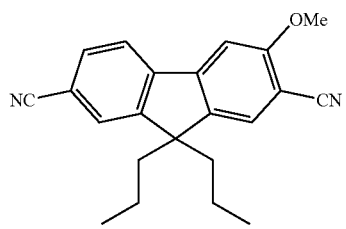

A mixture of 2,7-dibromo-9,9-dipropyl-3-methoxyfluorene (83 g, 0.19 mol), and copper(I) cyanide (50 g, 0.56 mol) in anhydrous dimethylformamide (70.0 mL) was stirred under reflux and argon for 18 hours. The reaction was allowed to cool to 90° C. and treated with a solution of potassium cyanide (100 g) in water (350 mL). The resulting mixture was stirred rapidly for a further 4.5 hours. The granular product was collected by filtration, crushed, washed with water and dried. The tan colored solid was extracted from a soxhlet with methylcyclohexane. Cooling and seeding of the methylcyclohexane extract afforded 2,7-dicyano-9,9-dipropyl-3-methoxyfluorene upon filtration (62.6 g; yield 99%).

Analytical Results were as follows: Melting point ° C. 163-167° C. Analytical Calculation: C, 79.97; H, 6.71; N, 8.48. Found: C, 80.33; H, 6.58; N, 8.51%.

Step 4. Preparation of 9,9-Dipropyl-3-methoxyfluorene-2,7-dicarboxylic Acid

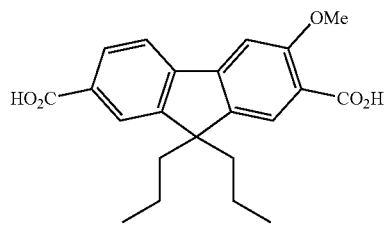

To a stirred solution of potassium hydroxide (61 g, 0.95 mol, 87% purity) in water (1400 mL) was added 2,7-dicyano-9,9-dipropyl-3-methoxyfluorene (62.6 g, 0.19 mol) and 1-propanol (350 mL). The mixture was heated under reflux for 70 h and then allowed to cool to room temperature. The mixture was treated with 6.0M HCl (180 mL), stirred for 1 h and the resulting solid collected, washed with water and dried to afford 9,9-dipropyl-3-methoxyfluorene-2,7-dicarboxylic acid (66.5 g; yield 95%).

Analytical Results were as follows: Melting point 282-285° C. dec. Analytical Calculation: C, 71.72; H, 6.57; N, 0.00%. Found: C, 70.81; H, 6.42; N, 0.19%. FTIR (KBr): 3300 br (OH), 3060 br sh, 2930 s, 2875 (Me), 2640 br, 2540 br, 1720 s & 1675 vs (C=O), 1605 (C=C), 1578, 1430 s, 1270 s, 1222 s, 1210 s, 1170 (Ar—O), 1026 (Me—O), 910 w, 840 w, 780 w, 725 w. $^1H$ NMR (60 MHz, 10% in pyridine-$d_5$): 0.75 (1 OH, br s, $CH_3CH_2CH_2$), 2.1 (4H, br s, $CH_3CH_2CH_2$), 4.05 (3H, s, $OCH_3$), 7.87 (1H, d, $J_{1-4}$=2 Hz, H4), 8.15 (1H, d, $J_{5=6}$=8 Hz, H5), 8.51 (1H, dd, $J_{6-8}$=3 Hz, H6), 8.70 (2H, br s, H1, H8), 14.29 (2H, s, COOH).

Step 5. Preparation of N,N'-Bis(2-hydroxy-5-methylphenyl)-9,9-dipropyl-3-methoxyfluorene-2,7-dicarboxamide

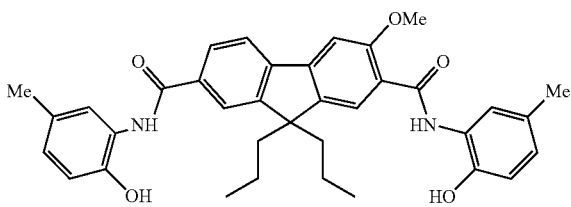

A solution of 9,9-dipropyl-3-methoxyfluorene-2,7-dicarboxylic acid (43 g, 0.117 mol), thionyl chloride (30.0 mL, 48.9 g, 0.41 mol), p-dioxane (430 mL) and N-methylpyrrolidinone (2.0 mL), under argon, was stirred and heated under reflux for 3 h. Concentration of the reaction mixture by distillation of p-dioxane (50.0 mL) precipitated the diacid dichloride intermediate. The dark diacid dichloride solution, over a period of 20 min., was added to a cooled (0° C.) stirred solution of 2-amino-4-methylphenol (30.8 g, 0.25 mol), anhydrous piperidine (21.0 mL) and p-dioxane (200 mL) under argon. The resulting mixture was stirred at room temperature for 18 h then treated with water (50.0 mL) to dissolve the pyridinium chloride. The mixture was then added to 1.8 L of water, with stirring, to form the crude product as a granular solid, which was collected, washed with 50% methanol/water (500 mL), and dried to afford N,N'-bis(2-hydroxy-5-methylphenyl)-9,9-dipropyl-3-methoxyfluorene-2,7-dicarboxamide (77.2 g).

Analytical Results were as follows: M. pt. 150-170° C. dec.

Step 6. Preparation of 2,7-Bis(5-methylbenzoxazol-2-yl)-9,9-dipropyl-3-methoxyfluorene.

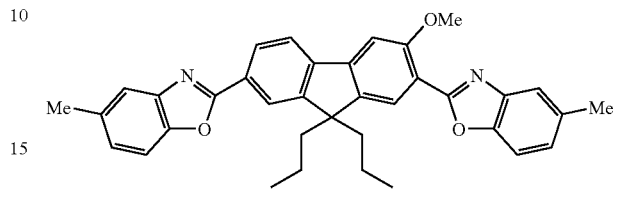

A mixture N,N'-bis(2-hydroxy-5-methylphenyl)-9,9-dipropyl-3-methoxyfluorene-2,7-dicarboxamide (76.7 g, 0.133 mol), powdered boric acid (1.8 g) and (750 mL) stirred under argon was slowly heated to reflux allowing water to be distilled. After cooling overnight the resulting mixture was further distilled to remove diethylene glycol dibutyl ether (600 mL). The residual mixture was added to methanol (500 mL) causing precipitation of crude product. The mixture was diluted with water (100 mL) and cooled to −20° C. for 18 h. The mixture was filtered and the solid washed with methanol to afford crude product (51.4 g; m. pt. 205-230° C.). Purification by soxhlet extraction with hexane yielded 2,7-Bis(5-methylbenzoxazol-2-yl)-9,9-dipropyl-3-methoxyfluorene (34.6 g; yield 48%).

Analytical Results were as follows: M. pt. 240-248° C.

Step 7. Preparation of 2,7-Bis(5-methylbenzoxazol-2-yl)-9,9-dipropyl-3-hydroxyfluorene

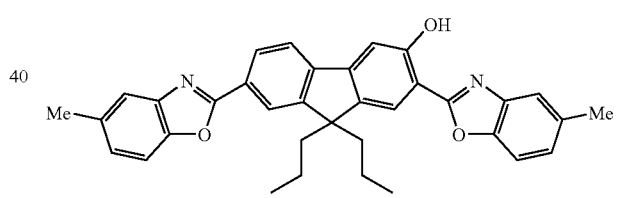

A mixture of a solution of 2,7-bis(5-methylbenzoxazol-2-yl)-9,9-dipropyl-3-methoxyfluorene] (34.6 g, 0.0638 mol) and 2,4,6-collidine (250 mL) that was prepared under argon by stirring and heating to 95° C. To this solution, dry lithium iodide (14.9 grams, 0.111 mol) was added and the resulting mixture was heated to reflux for 30 minutes and then allowed to cool to room temperature. The reaction was quenched with a mixture of concentrated HCl (167 mL), water (300 mL) and ice (500 g). The product was collected and washed with a minimum of water and methanol to afford upon drying crude product (40 g). Purification by extraction from of acidic alumina (3 cm$^3$) on Ace-Kauffman column with methylcyclohexane gave 2,7-bis(5-methylbenzoxazol-2-yl)-9,9-dipropyl-3-hydroxyfluorene (24.93 g, yield 74%).

Analytical Results were as follows: M. pt. 291-293° C. $^1H$ NMR (300 MHz, CDCl$_3$): 0.71 (10H, br s, $CH_3CH_2CH_2$), 2.1 (4H, br s, $CH_3CH_2CH_2$), 2.5 (6H, br s, ArCH$_3$), 7.17-8.28 (11H, m, ArH. $^{13}$C NMR (300 MHz, CDCl$_3$): 14.80 ($CH_3CH_2CH_2$), 17.6.9 ($CH_3CH_2CH_2$), 21.97 ($CH_3Ar$), 43.24 ($CH_3CH_2CH_2$), 55.61 (ArCAr) and 109.12-163.90 (aromatic C).

Reaction Scheme Example 2
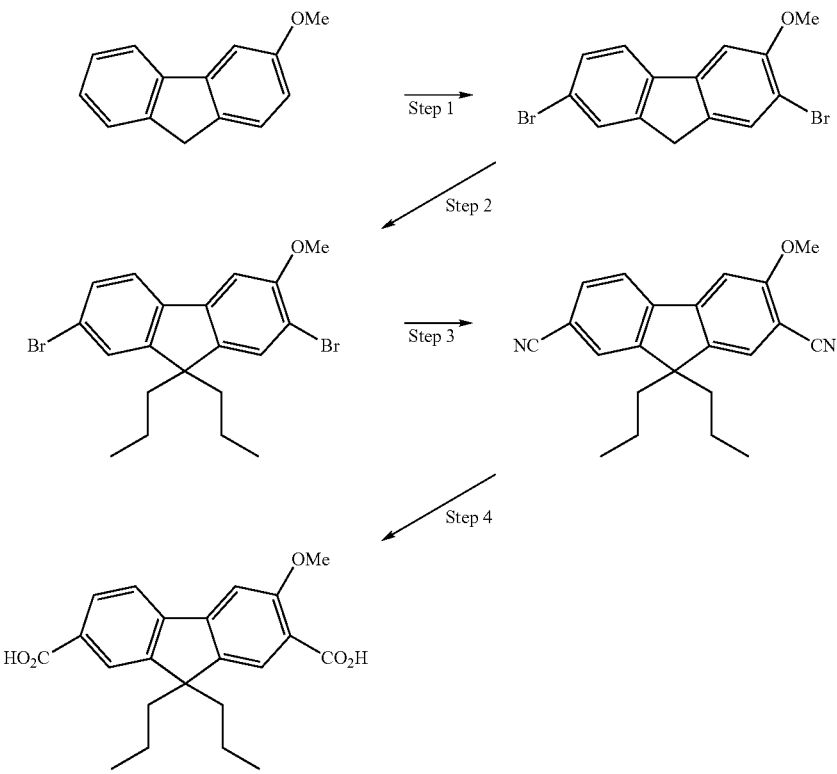
Reaction scheme for Example 2 (continued from step 4 supra):
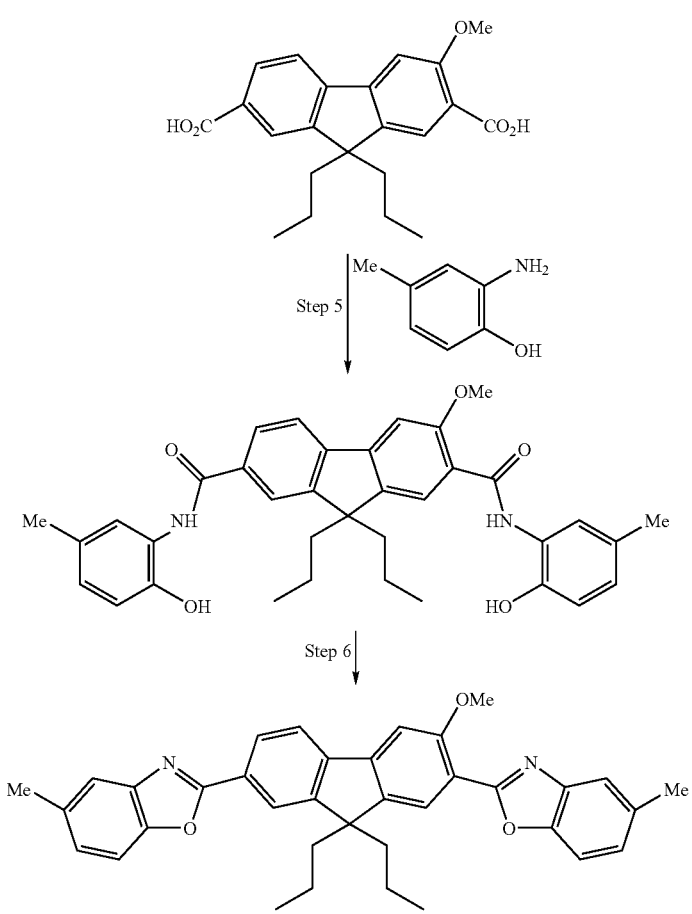

Preparation and Testing of Optical Objects

EXAMPLE 3

Preparation of Optical Objects According to Invention

Two 1.65 mm polycarbonate test articles (UV400 #1 and UV400 #2) comprising polycarbonate blended with an absorber of the invention were prepared. More specifically polymer blend containing FCR2407 polycarbonate (commercially available from Bayer) and the UV absorber 2,7-Bis(5-methylbenzoxazol-2-yl)-9,9-dipropyl-3-hydroxyfluorene (prepared in as set forth in Example 2) was prepared by admixing the polycarbonate and the UV absorber in a concentration of 0.22% (w/w). Optical flats were prepared by charging an injection molding apparatus with the polymer blend.

EXAMPLE 4

Comparative Tests of Optical Articles

The UV400 #1 and UV400 #2 articles exhibited an integrated absorbence of >99.9% between 370-400 nm (99.9% at 400 nm), with a yellow index of 2.7-2.8. These values compared to two control Essilor Tan lens (#1 and #2),. The Essilor Tan lenses are a UV380 product, which as a 1.8 mm flat gave 90-92% absorbance with a yellow index of 2.6-2.8. Generally, a yellow index of 2.6 to 2.8 is an acceptable minimum for commercial products.

Results of the comparison of the articles according to the invention with TAN #1 and TAN #2 are summarized in Tables 1-3 below, and the corresponding figures.

TABLE 1

| Sample | Photopic % | | | | | Scotopic % | | | | |
|---|---|---|---|---|---|---|---|---|---|---|
|  | Pre | 60 h | 120 h | 180 h | 240 h | Pre | 60 h | 120 h | 180 h | 240 h |
| TAN #1 | 91.7 | 91.5 | 92.0 | 91.2 | 90.9 | 90.9 | 90.8 | 91.3 | 90.5 | 90.1 |
| TAN #2 | 92.7 | 91.3 | 92.4 | 92.2 | 92.4 | 92.1 | 90.7 | 91.7 | 91.5 | 91.6 |
| UV400 #1 | 87.3 | 88.5 | 87.4 | 87.4 | 87.4 | 86.5 | 87.2 | 85.9 | 85.7 | 85.5 |
| UV400 #2 | 87.8 | 88.6 | 88.1 | 87.8 | 88.3 | 87.1 | 87.4 | 86.7 | 86.2 | 86.4 |

Figure 2:
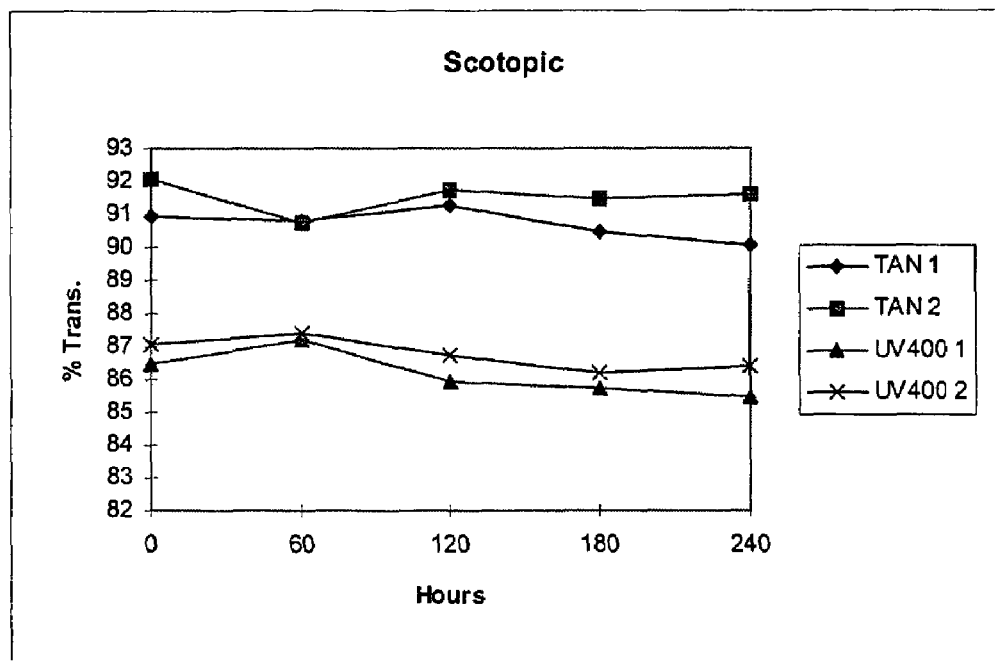
FIG. 2 is a graph of scotopic comparative data shown in Table 1.

FIG. 1 and FIG. 2 are graphs depicting the data shown in Table 1.

TABLE 2

| Sample | Integrated UV Transmission[1] | | | | | Yellowness Index | | | | |
|---|---|---|---|---|---|---|---|---|---|---|
|  | Pre | 60 h | 120 h | 180 h | 240 h | Pre | 60 h | 120 h | 180 h | 240 h |
| TAN #1 | 8.59 | 9.76 | 9.65 | 9.82 | 9.75 | 2.84 | 2.84 | 2.77 | 2.91 | 3.34 |
| TAN #2 | 10.23 | 10.76 | 10.85 | 11.00 | 11.30 | 2.69 | 2.75 | 2.77 | 2.93 | 3.03 |
| UV400 #1 | 0.06 | 0.27 | 1.34 | 2.75 | 4.28 | 2.85 | 2.85 | 6.12 | 6.84 | 7.70 |
| UV400 #2 | 0.06 | 0.30 | 1.30 | 2.80 | 4.44 | 2.62 | 2.65 | 6.02 | 6.80 | 7.64 |

Figure 3:
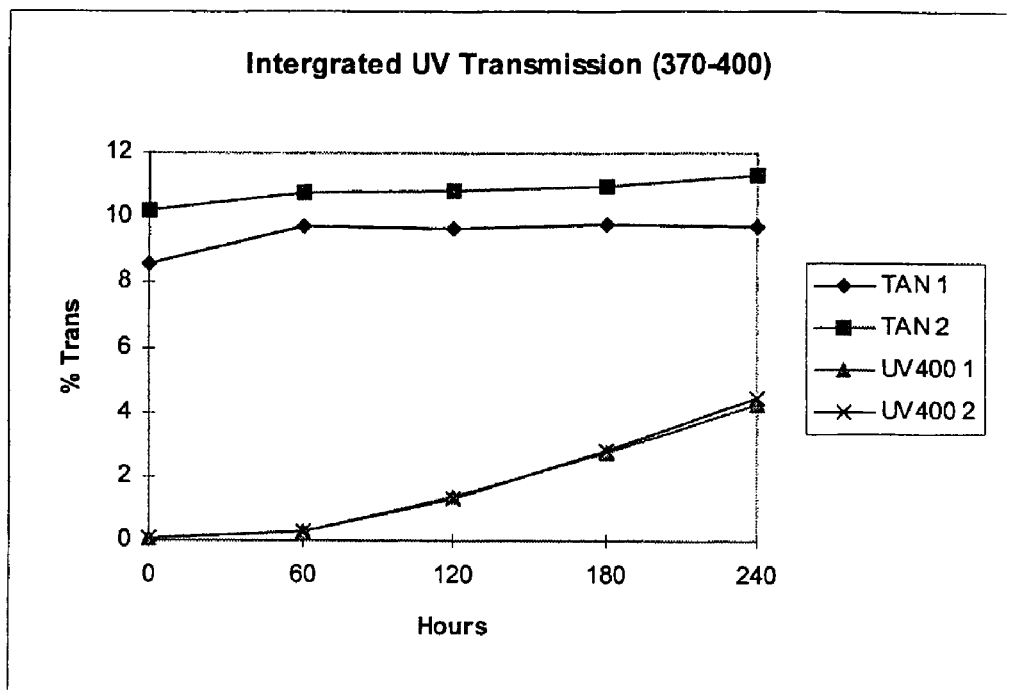
FIG. 3 is a graph of integrated UV transmission comparative data in Table 2.
Figure 4:
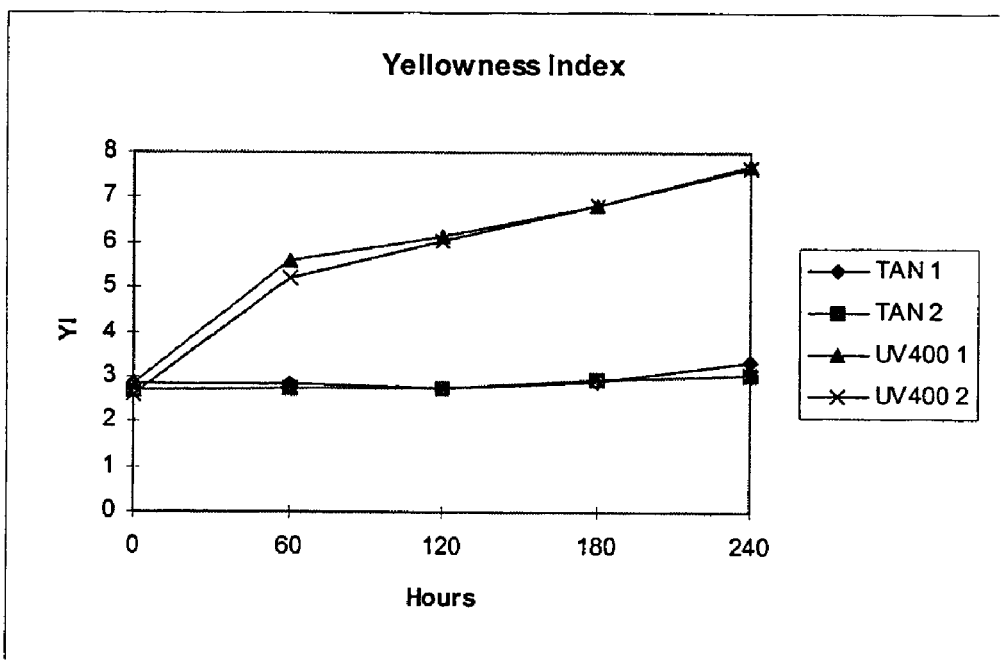
FIG. 4 is a graph of the Yellowness index comparative data in Table 2.

FIG. 3 and FIG. 4 are graphs depicting the data shown in Table 2.

TABLE 3

|  | Transmission at 380 nm | | | | | Transmission at 400 nm | | | | |
|---|---|---|---|---|---|---|---|---|---|---|
| Sample | Pre | 60 h | 120 h | 180 h | 240 h | Pre | 60 h | 120 h | 180 h | 240 h |
| TAN #1 | 0.010 | 0.016 | 0.015 | 0.017 | 0.019 | 18.70 | 20.80 | 20.60 | 20.90 | 20.7 |
| TAN #2 | 0.023 | 0.025 | 0.025 | 0.028 | 0.035 | 21.50 | 22.50 | 22.60 | 22.80 | 19.9 |
| UV400 #1 | 0.020 | 0.018 | 0.007 | 0.009 | 0.008 | 0.04 | 0.27 | 1.85 | 4.28 | 7.15 |
| UV400 #2 | 0.017 | 0.017 | 0.009 | 0.007 | 0.008 | 0.04 | 0.30 | 1.78 | 4.37 | 7.43 |

Figure 5:
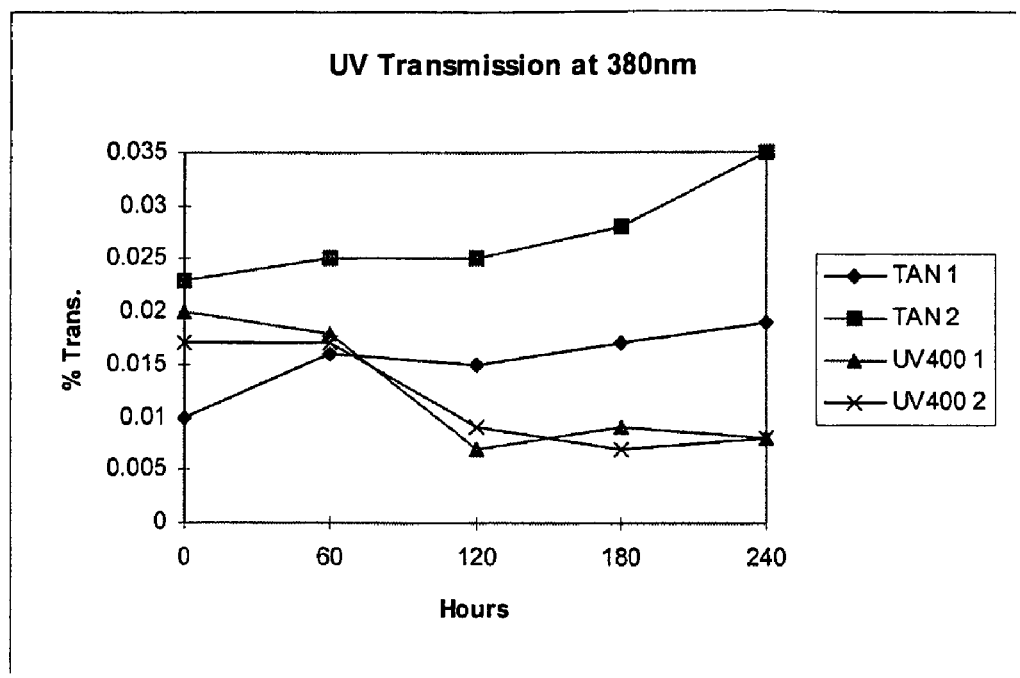
FIG. 5 is a graph of U transmission at 380 nm comparative data in Table 3.
Figure 6:
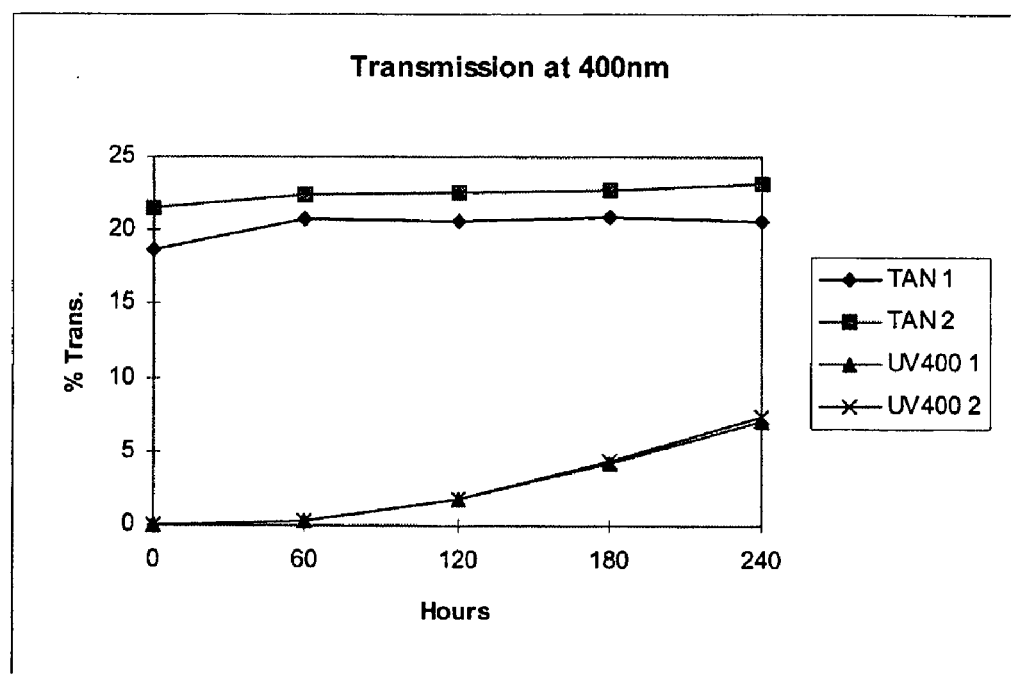
FIG. 6 is a graph of UV transmission data comparative data in Table 3.

FIG. 5 and FIG. 6 are graphs depicting the data shown in Table 3.

The data in Table 4 show the advantages of FCR2407 polycarbonate commercially available from Bayer doped with 2,7-Bis(5-methylbenzoxazol-2-yl)-9,9-dipropyl-3-hydroxyfluorene of the present invention (UV400 #1) compared to the undoped commercially available polycarbonate, with regard to UV blocking in the 370-400 nm region.

TABLE 4

Integrated Transmission (370-400 nm)

| | Concentrated g/Kg | Integrated Transmission 370-400 nm (%) |
|---|---|---|
| UV400 #1 | 0.22 | 0.023 |
| FCR2407 | — | 31.924 |

Data in Table 5 show how UV400 #1 compares with a commercially available heavily doped UV blocking polycarbonate (OQ4620) (commercially available from General Electric) with regard to transmission at 400 nm and the yellow index.

TABLE 5

Yellow Index

| | Concentrated g/Kg | Transmission at 400 nm (%) | Yellow Index |
|---|---|---|---|
| UV400 #1 | 0.22 | 0.024 | 2.58 |
| OQ4620 | — | 0.000 | 8.29 |
| FCR2407 | — | 58.7 | 0.27 |

EXAMPLE 5

Comparative Extinction Coefficient Studies

Comparative extinction coefficient studies were conducted to determine the extinction coefficient of UV absorbers made according to the invention with SEESORB 701 (2-(2-hydroxy-5-methylphenyl)-2H-benzotriazole) and SEESORB 102 (2-hydroxy-4-octyloxybenzophenone) which are commercially available UV absorbers sold by, for example, Shipro Kasei Kaisha. These compounds are well known to those of skill. The optical density measurements of 1,4-Bis (9,9-dipropyl-9H-fluoreno[3,2-d]oxazol-2-yl)-2-hydroxyphenyl, 2,7-Bis(5-methylbenzoxazol-2-yl)-9,9-dipropyl-3-hydroxyfluorene, SEESORB 702, and SEESORB 102 was taken in solution on a common UV/is spectrophotometer. Extinction coefficients are a common measure of absorbers and dyes to indicate their strength at a chosen wavelength. In the context of measuring the benefits of the invention, extinction coefficients determine the prominent and relevant absorbance maxima in the UV region. The table shows the claimed materials to be both significantly shifted towards the 400 nm mark and also to be significantly stronger absorbers at those wavelengths, when compared to the two SEESORB products

TABLE 6

Comparative Extinction Coefficient

| | λmax (nm) | Extinction Coeff. (solvent) | Solvent |
|---|---|---|---|
| 1,4-Bis(9,9-dipropyl-9H-fluoreno[3,2-d]oxazol-2-yl)-2-hydroxyphenyl | 402 380 362 | 67000 73500 42500 | Toluene |
| 2,7-Bis(5-methylbenzoxazol-2-yl)-9,9-dipropyl-3-hydroxyfluorene | 399 378 340 | 65500 63500 33400 | Toluene |
| SEESORB 701 | 298 340 | 14300 16600 | Chloroform |
| SEESORB 102 | 289 327 | 15200 10800 | Chloroform |

What is claimed is:
1. A compound having one of the following formulae:

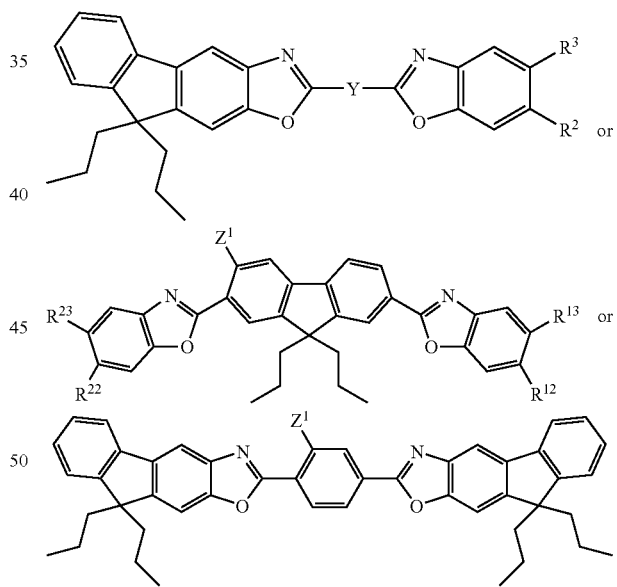

wherein:
—$Z^1$ is —OH, —SH, a primary or secondary amine;
Y is an aromatic, carbocyclic or heterocyclic moiety substituted at least once with OH and optionally substituted with SH, primary, secondary or tertiary amine, nitro, nitroso, halogen, a substituted or unsubstituted, straight or branched $C_{1-22}$ alkyl, $C_{2-22}$ alkene, $C_{2-22}$ alkyne, phenyl, $C_{3-6}$ cycloalkyl;
$R^{22}$, $R^{23}$, $R^{12}$ and $R^{13}$ are independently a substituted or unsubstituted, straight or branched $C_{1-22}$ alkyl, $C_{2-22}$ alkene, $C_{2-22}$ alkyne, phenyl, $C_{3-6}$ cycloalkyl, or at least one of the pairs $R^{22}$ and $R^{23}$ or $R^{12}$ and $R^{13}$ forms an aromatic or non-aromatic 1 to 3 ring cyclic moiety;

$R^2$ and $R^3$ are independently a substituted or unsubstituted, straight or branched $C_{1-22}$ alkyl, $C_{2-22}$ alkene, $C_{2-22}$ alkyne, phenyl, $C_{3-6}$ cycloalkyl, or together form an aromatic or non-aromatic 1 to 3 ring cyclic structure.

2. The compound of claim 1, wherein Y is chosen from:

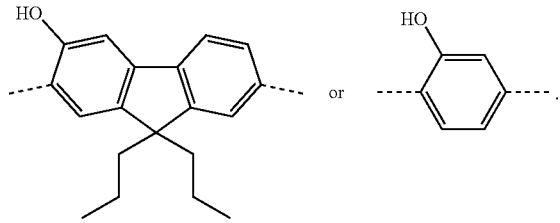

3. The compound of claim 1, wherein the compound has the formula:

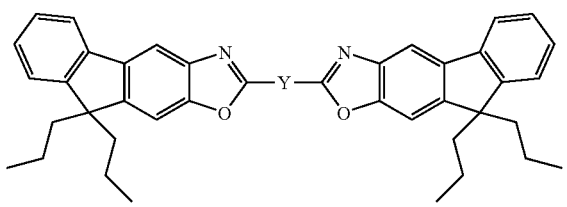

in which Y is an aromatic, carbocyclic or heterocyclic moiety substituted at least once with OH and optionally substituted with SH, primary, secondary or tertiary amine, nitro, nitroso, halogen, a substituted or unsubstituted, straight or branched $C_{1-22}$ alkyl, $C_{2-22}$ alkene, $C_{2-22}$ alkyne, phenyl, and $C_{3-6}$ cycloalkyl.

4. The compound according to claim 1, further defined as 1,4-bis(9,9-dipropyl-9H-fluoreno[3,2-d]oxazol-2-yl)-2-hydroxyphenyl of formula:

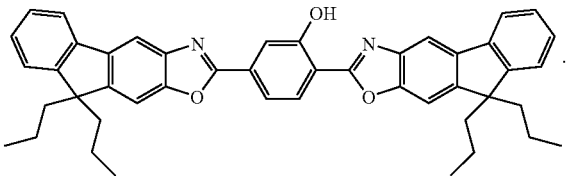

5. The compound according to claim 1, wherein at least one of the pairs $R^{22}$ and $R^{23}$ or $R^{12}$ and $R^{13}$ from:

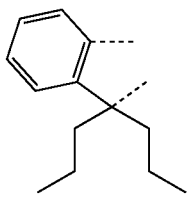

6. The compound according to claim 5, wherein the compound has the formula:

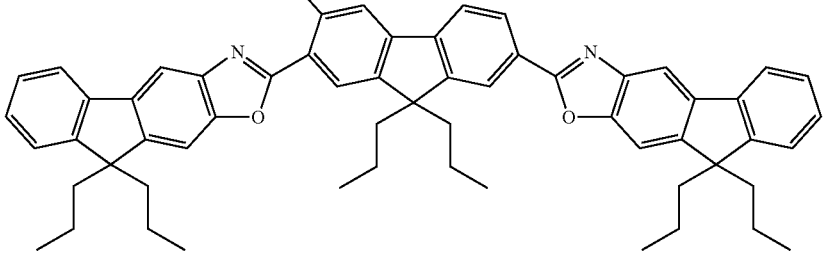

in which—$Z^1$ is —OH, —SH, a primary or secondary amine.

7. The compound according to claim 1, further defined as 2,7-bis(5-methylbenzoxazol-2-yl)9,9-dipropyl-3-hydroxyfluorene of formula:

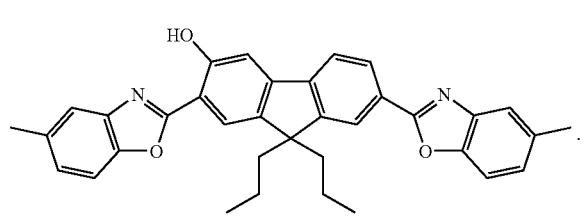

8. The compound according to claim 1 having the formula:

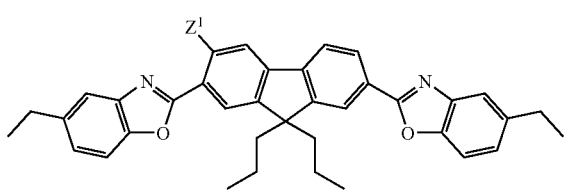

in which—$Z^1$ is —OH, —SH, a primary or secondary amine.

9. The compound according to claim 1, further defined as being incorporated into a polymer blend comprising a polymeric material.

10. The compound of claim 9, wherein said polymeric material is polycarbonate or CR-39®.

11. A method for manufacturing an optical lens, comprising molding the compound according to claim 9 into a desired shape to produce an optical lens.

12. The method of claim 11, wherein said molding step is injection molding.

13. The compound according to claim 1, further defined as being incorporated in an organic glass substrate.

14. The compound of claim 13, wherein the substrate is chosen from polycarbonates, substrates obtained by polymerization of alkyl methacrylates, allyl derivatives, allyl carbonates of linear or branched aliphatic or aromatic polyols, thio(meth)acrylics, thiourethanes, polyethoxylated aromatic (meth)acrylates, and polyethoxylated bisphenoate dimethacrylates.

15. The compound of claim 13, wherein the substrate is obtained by polymerization of ethylene glycol bis(allyl carbonate).

16. A method comprising the steps of preparing an intermediate compound of formula:

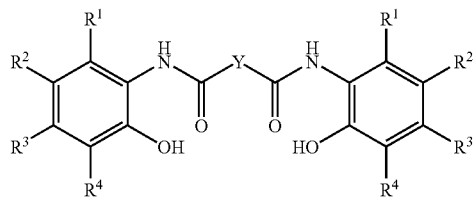

and reacting said compound under suitable conditions and with suitable reagents to form a compound of formula:

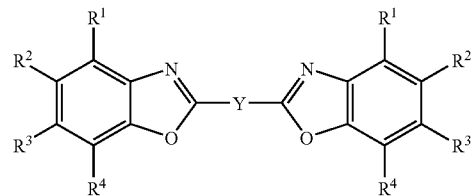

wherein:

Y is an aromatic or nonaromatic cyclic structure optionally substituted at least once with OH, SH, H, $C_{1-22}$ alkyl, $C_{2-22}$ alkene, $C_{2-22}$ alkyne, primary, secondary or tertiary amine, amino, nitro, nitroso, halogen; and $R^1$, $R^2$, $R^3$ and $R^4$ are independently selected from H, alkyl ($C_1$-$C_8$), alkoxy ($C_1$-$C_8$), acyl (—C(O)R; R=alkyl $C_1$-$C_8$), acetoxy (—OC(O)R; R=alkyl $C_1$-$C_8$), carboxylic acid and esters (—CO$_2$R=H or alkyl of $C_1$-$C_8$), amine (NR$_2$; R=H or alkyl $C_1$-$C_8$), nitro, nitroso, cyano, halogen (Cl, Br, I or F), substituted or unsubstituted aryl, substituted or unsubstituted heteroaryl, amide (—C(O)NR$_2$R=H or alkyl $C_1$-$C_8$), substituted or unsubstituted heterocylic, substituted or unsubstituted benzannulated heterocyclic and substituted or unsubstituted arylannulated or wherein heterocylic, or wherein:

$R^1$ and $R^2$ or $R^2$ and $R^3$ or $R^3$ and $R^4$ together form a carbocyclic ring, substituted or unsubstituted and fused carbocyclic ring, substituted or unsubstituted benzannulated carbocyclic and substituted or unsubstituted arylannulated carbocyclic.

17. The method of claim 16, comprising the steps of preparing an intermediate compound of formula:

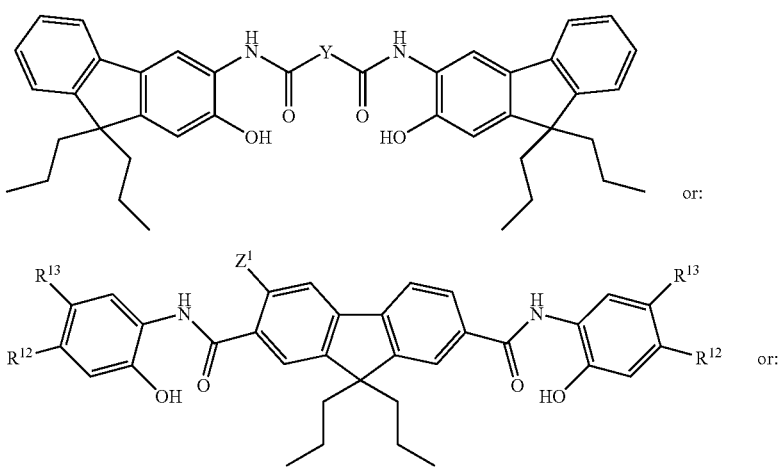

-continued

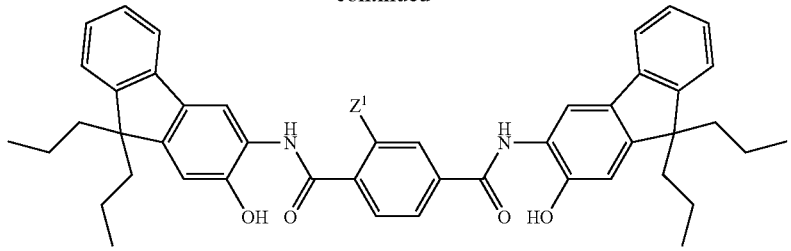

and reacting said compound under suitable conditions and with suitable reagents to form, respectively, a compound of formula:

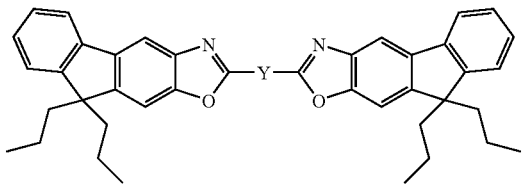

or:

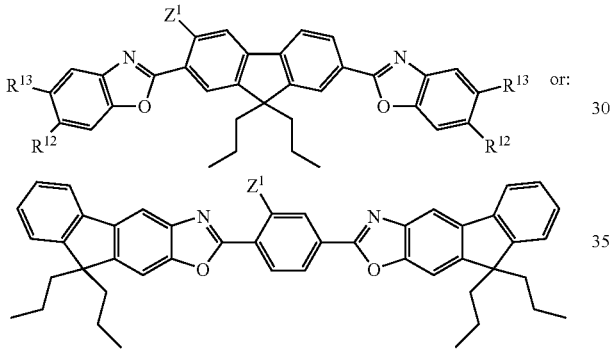

wherein:
- $-Z^1$ is —OH, —SH, a primary or secondary amine;
- Y is an aromatic, carbocyclic or heterocyclic moiety substituted at least once with OH and optionally substituted with SH, primary, secondary or tertiary amine, nitro, nitroso, halogen, a substituted or unsubstituted, straight or branched $C_{1-22}$ alkyl, $C_{2-22}$ alkene, $C_{2-22}$ alkyne, phenyl, $C_{3-6}$ cycloalkyl;
- $R^{12}$ and $R^{13}$ am independently a substituted or unsubstituted, straight or branched $C_{1-22}$ alkyl, $C_{2-22}$ alkene, $C_{2-22}$ alkyne, phenyl, $C_{3-6}$ cycloalkyl, or together form an aromatic or non-aromatic 1 to 3 ring cyclic moiety.

18. The method of claim 16, wherein Y is chosen from:

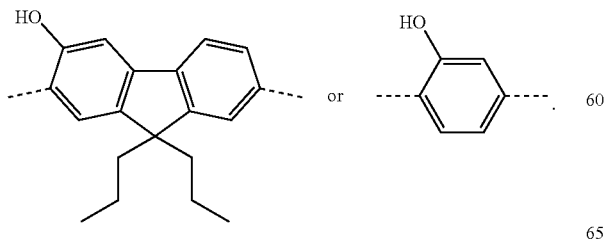

19. The compound of claim 3, wherein Y is chosen from:

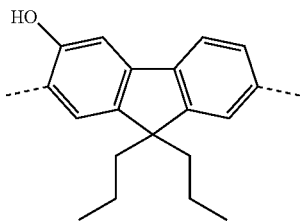 or 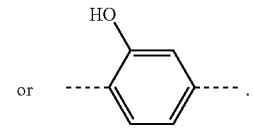

20. The method of claim 16, wherein $Z^1$ is OH.

* * * * *

UNITED STATES PATENT AND TRADEMARK OFFICE
CERTIFICATE OF CORRECTION

PATENT NO. : 7,713,452 B2
APPLICATION NO. : 10/565414
DATED : May 11, 2010
INVENTOR(S) : Joel M. Kauffman et al.

It is certified that error appears in the above-identified patent and that said Letters Patent is hereby corrected as shown below:

In claim 5, column 22, line 12, delete "from" and insert --form-- therefor.

In claim 6, column 22, lines 26-37, delete chemical drawing and insert

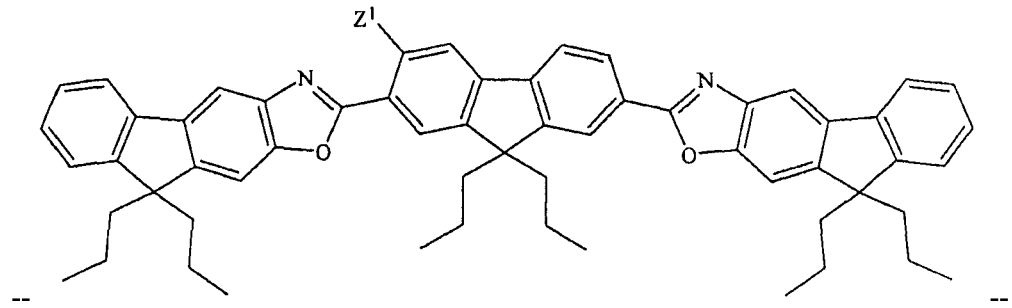

therefor due to overlapping of chemical drawing and text of claim in printed patent.

In claim 7, column 22, line 41, delete "2,7-bis(5-methylbenzoxazol-2-yl)9" and insert --2,7-bis(5-methylbenzoxazol-2-yl)-9-- therefor.

In claim 16, column 24, line 19, delete "alky" and insert --alkyl-- therefor.

In claim 16, column 24, line 27, delete "heterocylic" and insert --heterocyclic-- therefor.

In claim 16, column 24, line 29, delete "or wherein heterocylic" and insert --heterocyclic-- therefor.

In claim 17, column 25, line 50, delete "am" and insert --are-- therefor.

Signed and Sealed this

Tenth Day of August, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,713,452 B2 | Page 1 of 1 |
| APPLICATION NO. | : 10/565414 | |
| DATED | : May 11, 2010 | |
| INVENTOR(S) | : Joel Kauffman et al. | |

It is certified that error appears in the above-identified patent and that said Letters Patent is hereby corrected as shown below:

In title page, item (73) Assignee, line 4, insert
--Joel Kauffman, Wayne, PA (US)--

Signed and Sealed this
Twenty-fourth Day of May, 2011

David J. Kappos
*Director of the United States Patent and Trademark Office*